US006730024B2

United States Patent
Freyre et al.

(10) Patent No.: US 6,730,024 B2
(45) Date of Patent: May 4, 2004

(54) METHOD AND APPARATUS FOR COLLECTING PATIENT COMPLIANCE DATA INCLUDING PROCESSING AND DISPLAY THEREOF OVER A COMPUTER NETWORK

(75) Inventors: Carlos V. Freyre, Miami, FL (US); Murat Kuru, Miami, FL (US); Roger K. Khouri, Key Biscayne, FL (US)

(73) Assignee: Brava, LLC, Coconut Grove, FL (US)

( * ) Notice: Subject to any disclaimer, the term of this patent is extended or adjusted under 35 U.S.C. 154(b) by 0 days.

(21) Appl. No.: 09/809,986

(22) Filed: Mar. 16, 2001

(65) Prior Publication Data

US 2002/0013516 A1 Jan. 31, 2002

Related U.S. Application Data (63) Continuation-in-part of application No. 09/572,348, filed on May 17, 2000, now Pat. No. 6,514,200.

(51) Int. Cl.[7] .......................... A61B 5/00; A61B 5/103; A61F 5/00
(52) U.S. Cl. .................. 600/300; 128/904; 600/38; 600/587; 601/14
(58) Field of Search ................................ 600/300–301, 600/309, 305, 481–486, 500–503, 558–559, 587–592, 38–41; 128/898–897, 903, 904, 920–925; 601/14, 6, 11; 705/2–4; 702/19; 340/573.1

(56) References Cited

U.S. PATENT DOCUMENTS

| | | | | | |
|---|---|---|---|---|---|
| 5,695,445 | A | * | 12/1997 | Khouri | 600/38 |
| 5,827,180 | A | * | 10/1998 | Goodman | 600/300 |
| 5,947,901 | A | * | 9/1999 | Redano | 600/439 |
| 5,950,632 | A | * | 9/1999 | Reber et al. | 128/898 |
| 6,168,331 | B1 | * | 1/2001 | Vann | 400/472 |

FOREIGN PATENT DOCUMENTS

WO WO 02/00111 A1 * 1/2002 ............ A61B/5/00

* cited by examiner

*Primary Examiner*—Max F. Hindenburg
*Assistant Examiner*—Michael Astorino
(74) *Attorney, Agent, or Firm*—Thompson Coburn LLP (57) ABSTRACT

An apparatus and method for collecting and processing information relating to a patient's compliance with a recommended treatment protocol is provided. A portable medical device is adapted to be worn by a patient. The medical device has a control for automatically collecting and processing information relating to the patient's compliance with a recommended treatment protocol. A separate communications cradle is provided that is configured to connect to the control of the medical device. The cradle has a communications link to transmit the patient compliance information to a host.

28 Claims, 13 Drawing Sheets

MEMBER INFORMATION

BRAVA® GROWTH GRAPH

The BRAVA System Growth Graph compares your actual measurement against historical data. The green points are your actual breast volume in cubic centimeters (cc) as measured during your visits. The gray line illustrates the historical growth curve. The Y-axis indicates volume in cc and the X-axis indicates the date at which the measurement was taken. If you have followed the protocol treatment, your data points should coincide with the historical data.

☐ - Your actual breast volume
☐ - Low historical growth curve
☐ - Average historical growth curve
☐ - High historical growth curve

| Back to Main Menu |

METHOD AND APPARATUS FOR COLLECTING PATIENT COMPLIANCE DATA INCLUDING PROCESSING AND DISPLAY THEREOF OVER A COMPUTER NETWORK

CROSS REFERENCE TO RELATED APPLICATION

This application is a continuation-in-part of Ser. No. 09/572,348, now U.S. Pat. No. 6,514,200 filed May 17, 2000.

BACKGROUND OF THE INVENTION

There are various kinds of medical devices which may be prescribed by doctors for home use by a patient. Many of these are in the physical therapy area but may also include devices intended to provide a therapeutic regimen for the patient. One example of such a device includes a device developed and patented by one of the co-inventors hereof for enlarging soft tissue including a female's breasts. These devices are disclosed in the following patents: U.S. Pat. No. 5,695,445; U.S. Pat. No. 5,676,634; U.S. Pat. No. 5,662,583; U.S. Pat. No. 5,701,917 and U.S. Pat. No. 5,536,233. With this particular device, due to its personal nature, the patient may well choose to perform the prescribed regimen within the privacy of her own home. However, as this device has been developed for commercialization, a product has been designed and will be offered to the public which may be discreetly worn and be virtually undetectable in normal daily activities. With either of these choices, a patient must wear the device for some period of time and at specified vacuums in order to achieve the desired soft tissue enlargement. While it is entirely possible for a patient to manually keep track of and record her wearing times, vacuum pressure settings, and other events relating to her regimen such as unintentional loss of pressure, this requirement interferes with the convenience and intended simplicity of use which is highly desired in a personal product such as this. However, for more important medical reasons, it is highly desired to obtain accurate data relating to the patient's use of the medical device as such data may very well explain the success or failure that the patient achieves. Furthermore, more obstacles presented to a patient in connection with her use of a medical device would be expected to interfere with its use and the resulting patient compliance. There are even health and safety concerns which could be monitored more closely should the patient be more accurate in recording her compliance with her prescribed regimen.

As many of these medical devices are prescribed by physicians, the opportunity to collect reliable data is often times limited to those patient visits which occur at prescribed intervals. While in the doctor's office, the patient may be physically examined and tests made to determine how the patient is reacting to the use of the medical device. This may then be compared with the patient compliance data which the patient may have personally recorded and which may be less than 100% accurate. Therefore, a doctor or other medical professional does not reliably have accurate data with which to judge the efficacy of the prescribed regimen and thus reliably make adjustments in that regimen as he or she sees fit in order to improve the patient's condition. For example, with the breast enlargement device, when the patient visits the doctor's office, the breasts may be measured in order to ascertain any increase in size. However, the doctor must rely upon the patient's own data for compliance with the prescribed regimen. Therefore, while the doctor may measure marked under performance of the effect of the medical device on the patient, this may be entirely due to the patient's failure to follow the prescribed regimen which the doctor will be unable to detect as the patient for her own reasons may not provide correct or truthful data. Should the doctor have reliable patient compliance data then the doctor could feel comfortable in adjusting the regimen in order to increase the chances of success through the patient's use of the medical device.

There are still additional reasons which make it highly desirable to have accurate patient compliance data for a medical device used on an outpatient basis. One of these additional reasons includes the desirability of collecting data for a large group of individuals which may then be used to make considered judgments relating to the medical device efficacy and recommended regimen for optimal results. For these kinds of studies, accurate data is imperative and short of controlling the environment in which the patients exist for extended periods of time, the inventors are unaware of any prior art solution to this problem of collecting accurate patient compliance data for medical device use. Still another reason for collecting accurate data is that immediate feedback and positive re-enforcement may be provided to the patient which encourages her to follow the regimen. In other words, should a patient understand that compliance data will be accurately collected and made available, the patient will be encouraged to live up to her doctor's recommendations and know that the doctor will be able to follow her compliance and discuss her performance with her in a positive way. Furthermore, a patient may feel the psychological reward of knowing that she has complied with her doctor's prescribed regimen as well as achieving the expected results through use of the medical device. The doctor may also use this accurate compliance data in order to correct the patient should she not only under-use but over-use the device in an effort to achieve even greater results by increasing her wearing times or vacuum pressures beyond that which is recommended. This can help prevent unintended side effects through over-use of any medical device.

BRIEF SUMMARY OF THE INVENTION

To solve these and other shortcomings in the prior art, and in order to provide some of the advantages as noted above, the inventors herein have succeeded in designing and developing a method and apparatus for collecting patient compliance data as a medical device is used, a convenient and unobtrusive way to self-communicate that compliance data over any communications link such as the internet to a central location, and process that compliance data and make it available not only to the patient but also the medical professional in a secure but readily accessible form. More particularly, and as explained in the illustrative example of the breast enlargement device, the inventors have succeeded in designing and developing a portable controller or "smart box" which is battery operated and which controls a miniature vacuum pump included as part of the bra-like device in its intended commercial embodiment. A vacuum sensor is also provided for collecting data relating to the induced vacuum contained within the bra and a clock function such as might be provided by a micro-clock circuit or chip, times the duration of the vacuum applied by the medical device to the patient's breasts. With this device, vacuum pressures and durations may be readily collected as data and stored in onboard memory included as part of a microcomputer. Thus, patient compliance data for this particular device which would include vacuum pressures and durations is readily collected as the battery operated smart box is used to apply the vacuum through the bra-like medical device.

As the controller is battery operated, the patient will be conditioned through her experiences with other battery-operated devices such as cell phones and the like to place the controller into a cradle for charging of the on-board batteries. For convenience, the controller is preferably separable from the bra. The accompanying cradle includes not only an AC power cord for connection to a typical wall socket with the associated battery charger circuits for charging the controller's rechargeable batteries, but also a phone line connection and modem for downloading the data from the microcomputer memory and transmitting it over the telephone lines through either a dial-up connection, modem, or internet service provider to a central location which is preferably a digital processor device such as a computer server or the like. Thus, through this aspect of the invention, patient compliance data is automatically collected without patient intervention and the patient is conditioned to seek recharging of the batteries for the controller which when performed will preferably automatically "download" the data from the microcomputer through a modem to a central data processor. Alternatively, a command button or the like may be provided for the patient to push to force the download to occur.

Upon collecting data, the central data processor will preferably process the data and ready it for display. This processing may include nothing more than associating it with a particular patient but may also include further processing in order to present the data in various formats such as bar graphs, charts, and the like not only on an individual basis but also in comparison to other averages or patient data. This processed data is then preferably provided to one or more servers for display over a web site having a secure access. Various levels of security may be provided, as desired. For example, each patient may be given an individual password which allows her to access her own individual data. At the same time, a medical professional or doctor may be given a password which allows him or her to have access to the patients that he or she is treating. Lastly, a global password may be provided to one or more select individuals who oversee the entire web site and who may also oversee the conduct of the device use as well as its physiological impact on the various patients from a global perspective.

As briefly described, it is readily apparent that a novel method and apparatus have been described which provides a solution to many of the difficult problems surrounding independent and private use of a medical device in an outpatient setting including an unobtrusive way of collecting the data, making that data selectively available to individual patients as positive feedback and re-enforcement to encourage their compliance and display their progress, a vehicle for a doctor or other medical professional to monitor the progress of a patient on an individual basis as well a group of patients, and a methodology for monitoring a large number of patients, collecting and analyzing data relating to those patients, and making judgments with respect to the efficacy of a medical device as associated with particular regimens. All of this is achieved in a cost effective way using the power of the Internet as a tool for communicating between patient, doctor, and a central data collection monitor and service.

While the principal advantages and features of the present invention have been described above, a fuller understanding of the invention and its many various aspects may be attained through reference to the drawings and detailed description of the preferred embodiment which follows.

DETAILED DESCRIPTION OF THE PREFERRED EMBODIMENT

Figure 1:
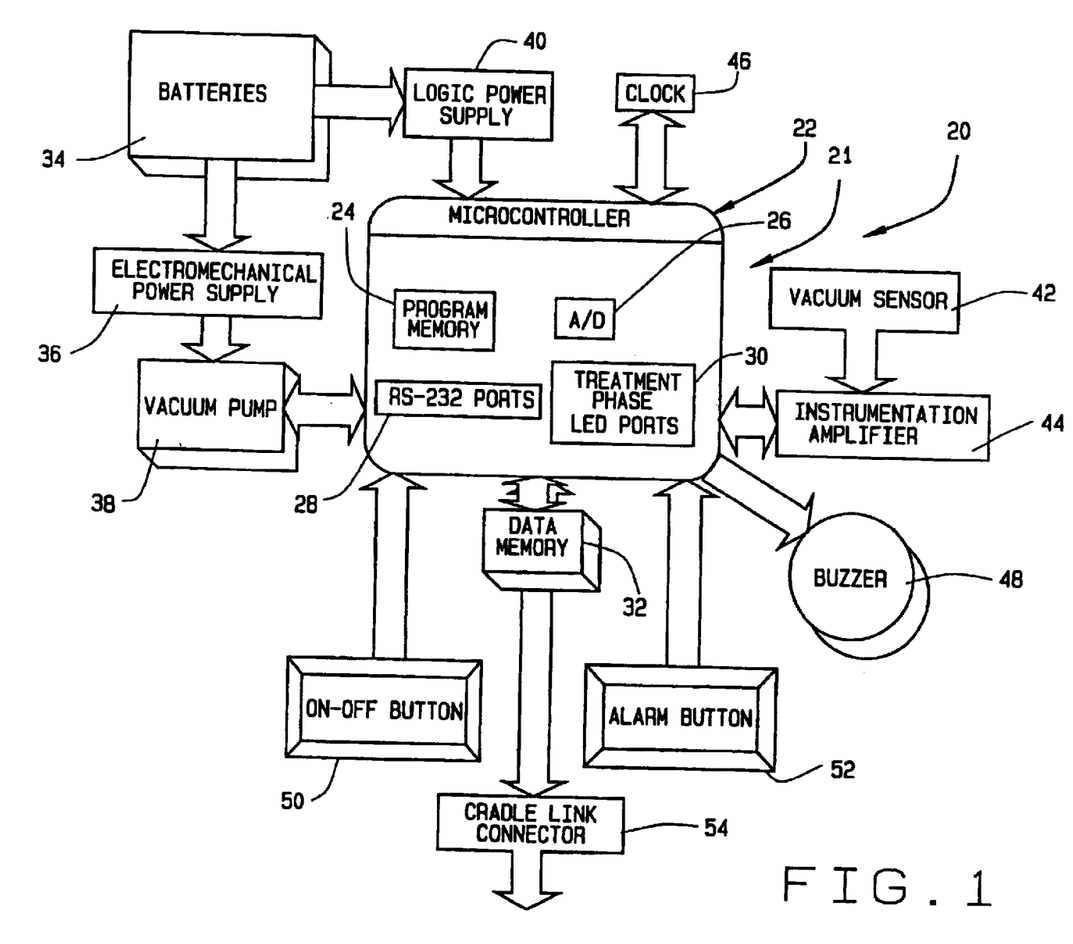
FIG. 1 is a block diagram of a controller or "Smartbox" for a medical device.
Figure 4:
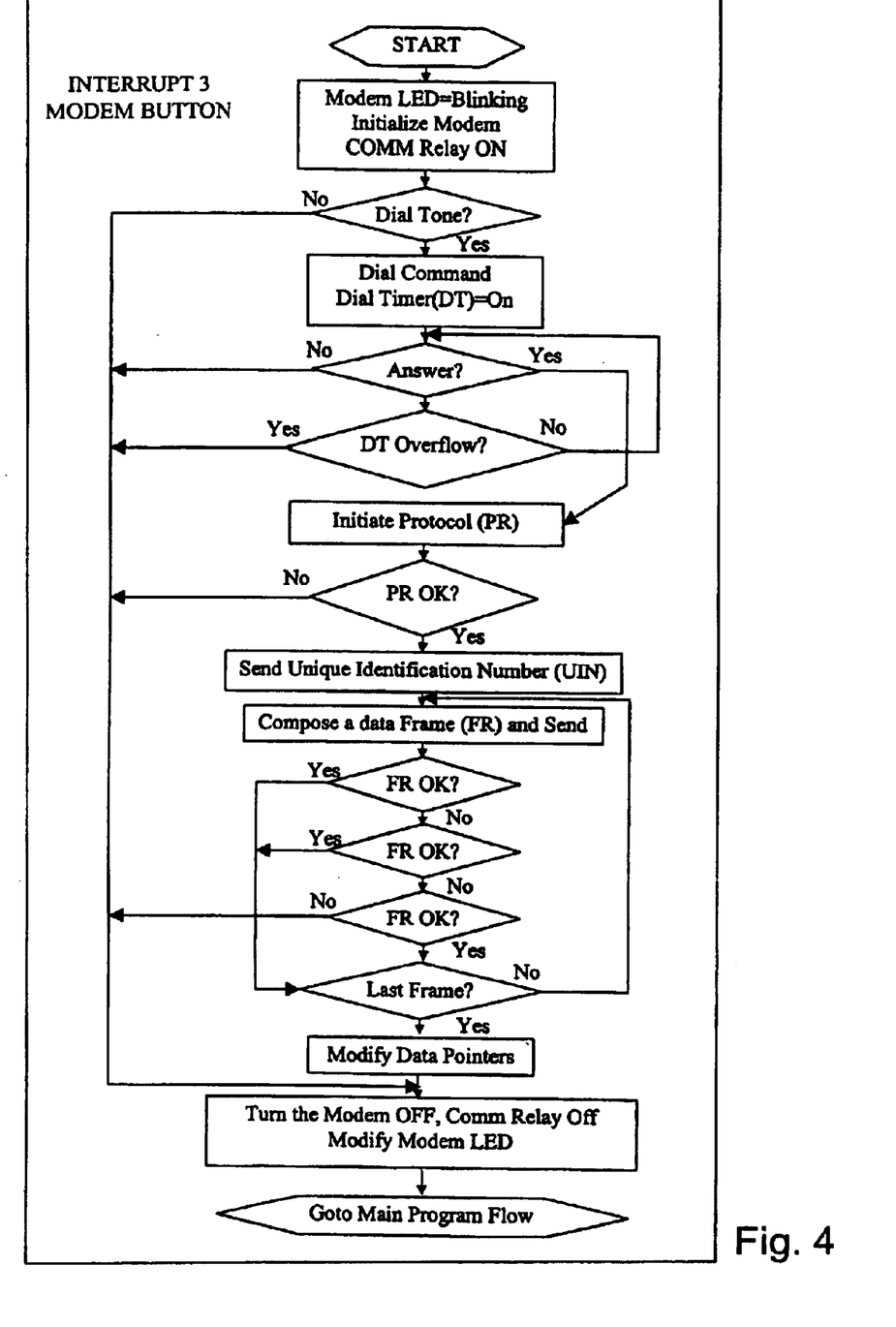
FIGS. 4–6 are flowcharts depicting examples of algorithms used in the medical device.
Figure 5:
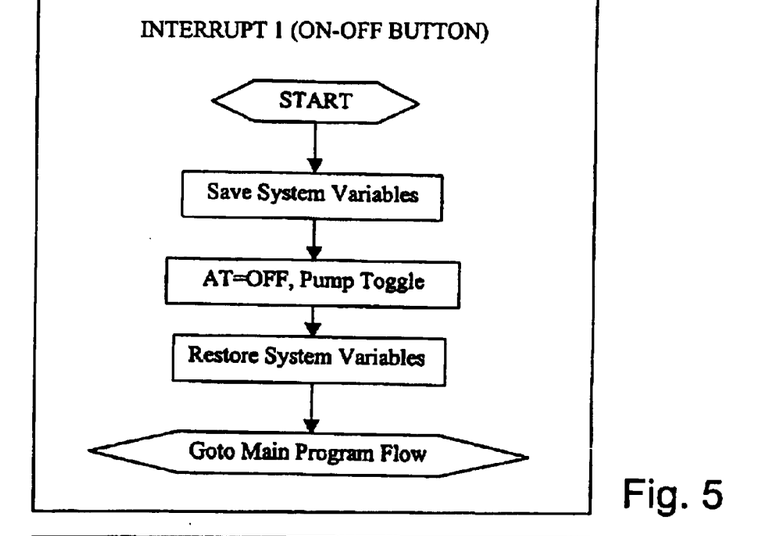
Figure 6:
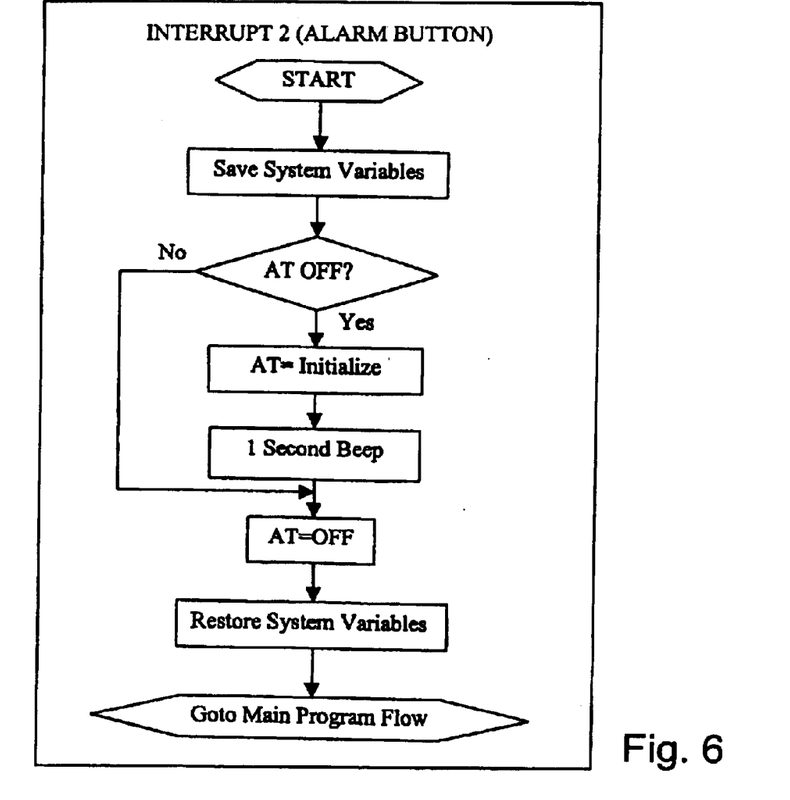

As shown in FIG. 1, the controller 20 is a self-contained battery operated unit which is portable and which is preferably detachable from the bra (not shown) having a pair of cups within which a vacuum is drawn in order to enlarge a female's breasts as is taught in the co-inventor's prior patents mentioned above, the disclosures of which are incorporated herein by reference. More particularly, the controller 20, which may be a microcontroller, includes at its heart a microcomputer 22 having a program memory 24 within which is stored software for controlling the operation of the controller. An example of such software is shown in the flowchart of FIGS. 4–6, although other application software may also be used to perform the functional tasks as described herein. The controller or microcontroller may have also an associated AID converter 26 as well as a plurality of RS-232 ports 28 for receiving and transmitting data, as is known by those of skill in the art. A plurality of LED ports 30 are preferably provided to provide data to the cradle (see below) to indicate the relative vacuum pressure at any particular time during the regimen. An associated data memory 32 stores the data collected by the microcomputer 22 and readies it for transmission as is explained below. Each Smartbox is preferably encoded with a UIN or Unique Identification Number for identifying it when data is downloaded to the central site, as explained below. This UIN is also preferably used to set up and identify the virtual patient folders so that data received at the central site is reliably associated with other patient data in what may be a disk drive or other memory where the virtual patient folder is maintained. The patient is then preferably given this UIN to use as part of her sign on so that she is reliably provided access to only her data file. This provides still another level of security for data collected using the present invention.

Also included in the controller 20 is a set of rechargeable batteries 34 which power an electromechanical power supply 36 for operating associated electromechanical devices including a vacuum pump 38. The batteries 34 also power the logic supply 40 which powers the microcomputer 22. A vacuum sensor 42 which may be a temperature compensated, calibrated differential vacuum sensor such as those produced by using Micro Electro Mechanical Systems (MEMS) Technology senses the vacuum within the domes and generates data which is amplified by an instrumentation amplifier 44 for communication to the microcomputer 22. This data is associated with timing data produced by a clock 46, which may be any appropriate electronic chip or circuit, such that the microcomputer collects not only the relative vacuum pressure but also its duration as the medical device is used. A buzzer 48 or other alarm device may be used to indicate to the patient that the vacuum seal has been breached, or for other conditions to provide feedback to the patient and permit her to adjust the device in order to insure its proper use. An on/off button 50 provides a master control for the controller and an alarm button 52 may be useful in disabling the buzzer 48 once the patient is alerted to the particular issue at hand, or to otherwise silence the alarm and prevent its becoming an embarrassment should the patient be wearing the device in a public area. A cradle link connector 54 provides an electromechanical linkage between the controller 20 and the cradle so that the two may be physically, electronically, and electrically interconnected as desired for battery recharge as well as data download.

In the preferred embodiment of the controller, the data memory 32 is sufficiently large to enable a continuous recording of 217 days worth of data by collecting one sample every ten minutes. This methodology may of course be modified as desired to meet specific applications. The rechargeable batteries 34 are preferably nickel metal hydride cells and as noted there are preferably two power conversion sub units on board for supplying power to electronic and electromechanical components The electronic components are chosen to be five volt components. However, as is known by those of skill in the art, the power unit may be readily modified for 3.3 volts or other lower operating voltages. The topology used for the logic power supply 40 is boost topology with 75% efficiency, The electromechanical power supply 36 is preferably programmable for different applications. In the present preferred embodiment example, a controlled vacuum is created inside the bra domes. Thus, a vacuum pump 38 is employed in the controller 20. For this application, power supply 36 uses the sepic topology for supplying voltages higher and lower than the battery voltages with a 55 to 70 percent efficiency. Nickel metal hydride battery cells are preferably used to avoid the inherent safety problems of lithium cells and to supply better power density than nickel cadmium cells. The programming for the microcomputer includes mermory handling routines, electromechanical device control routines, sensor measurement routines, serial communication routines for communication over the RS-232 ports 28, serial communication protocols for these same ports, and numerous mathematical functions for implementing algorithms, all which are well known by those of skill in the art and as partly exemplified in FIGS. 4–6. While the controller 20 of the preferred embodiment has been developed for maintaining a preselected vacuum range within the bra domes, collecting and recording measured vacuum values and duration in a non-volatile memory, communicating with the user by means of two momentary switch buttons (on/off and alarm) and an audible buzzer 48, calculating progress algorithms and transferring any and all patient compliance data to and from a base unit, it is envisioned that the controller 20 of the present invention may also be employed for other numerous patient data related applications requiring portability, small size, reliability and connectivity.

Figure 2:
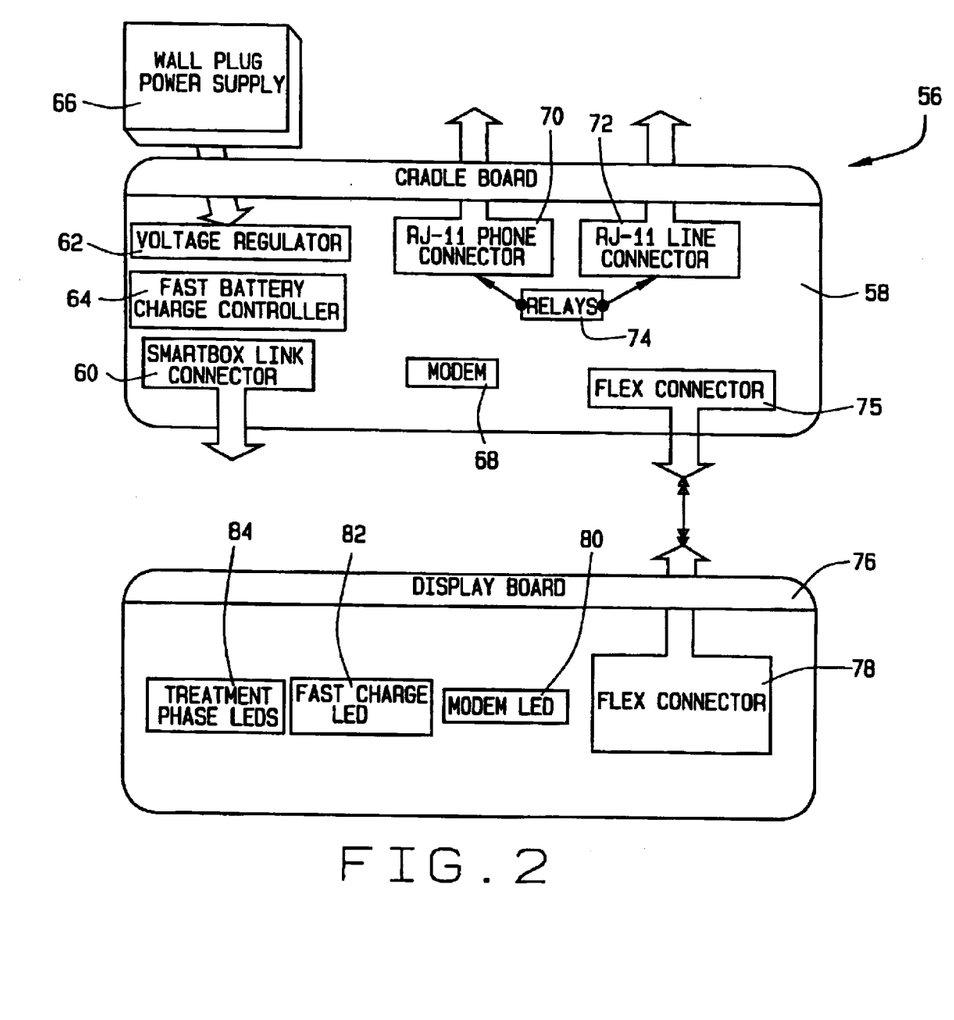
FIG. 2 is a block diagram of a cradle for receiving the controller.

Referring now to FIG. 2, a cradle 56 includes a cradle control board 58 having a smart box link connector 60 for connection to the smart box or controller 20 through its cradle link connector 54. Also, a voltage regulator 62 provides voltage to a fast battery charge controller 64 and is provided power by an AC plug-in 66 to provide the power for charging the batteries 34 carried on the controller 20 in a manner well known to those of skill in the art. The cradle board 58 also includes a modem 68 which may either be provided separately or as part of cradle board 58 and serves to transfer data over the RJ-11 phone connection 70, as known in the art. A second RJ-11 line connector 72 may be provided with switching relays 74 to allow the phone line to be shared with other appliances such as other phones, etc. A flex connector 75 connects the cradle board 58 to a display board 76. The display board 76 has a corresponding flex connector 78 and includes a modem LED 80 to indicate operation of the modem, a fast charge LED 82 to indicate charging action for the batteries, and treatment phase LEDs 84 to indicate to the user her treatment phases. For example, for the device of the preferred embodiment, the LEDs may indicate to the patient that she has worn the bra for a prescribed period of time at a prescribed vacuum during a specified number of days and thereby indicate that she is ready to go on to the next treatment regimen. Failure to move on means that the patient stays in the same treatment phase and must continue with that wear schedule until she successfully achieves the prescribed number of hours in a prescribed number of days.

In operation, the patient is typically expected to utilize the cradle daily for recharging the Smartbox batteries, although daily recharging is not required. However, when connected, the patient may also observe her treatment phases through the set of treatment phase LEDs 84, which may be six LEDs indicating to the patient her progress against her prescribed treatment regimen as explained above, and to also transfer patient compliance data over the modem. Connection parameters for the modem are preferably stored and programmed into the modem memory. This information may be overridden by the controller should the need arise such as for example to change the dial in connection phone number for the modems. The communication protocol is a modified E1381-95 to facilitate longer modem delays. The data may be preferably transferred in blocks with parity checks to maintain data integrity.

Figure 3:
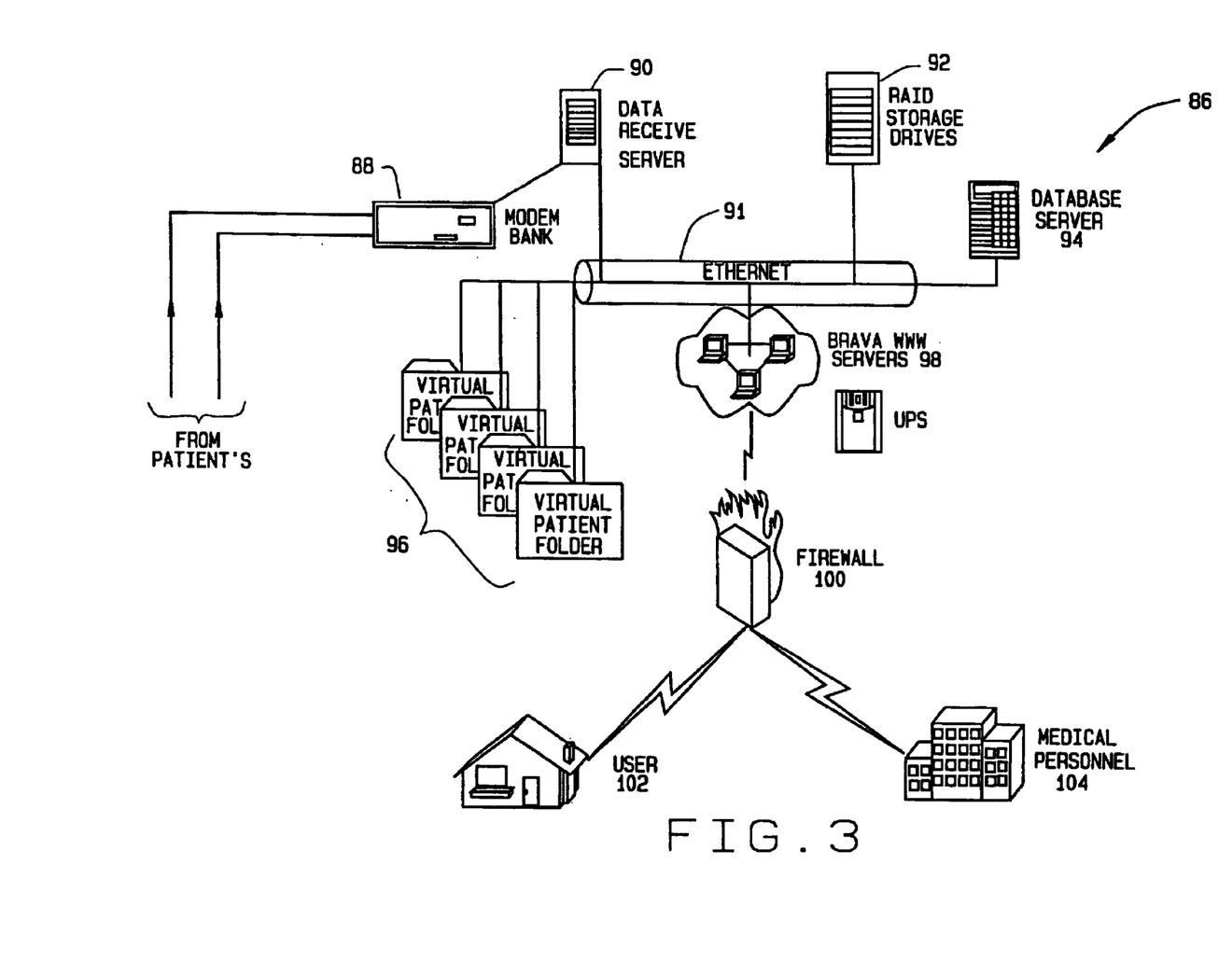
FIG. 3 is a schematic diagram of a computer network including the Internet for receiving data, processing data, and displaying it on a secure web site.

Referring now to FIG. 3, a computer network such as a local area network (LAN) 86 is preferably provided at a central location for collecting the data through a bank of modems 88 and supplying that data to a data receive server 90 for processing thereof. An ethernet network 91 is shown for interconnecting the data receive server 90 with a bank of raid storage drives 92 and a data base server 94. The data base server 94 may perform the data processing of data received by data receive server 90 depending upon the data handling requirements. A set of virtual patient folders 96 are established and may be stored conveniently at any location in the network 86 and which contain the data files for the individual patients providing data relating to their compliance. A plurality of web servers 98 are provided and provide a secure access for this processed data over the Internet through a firewall 100 for access by individual patients 102 and medical personnel 104.

Figure 7:
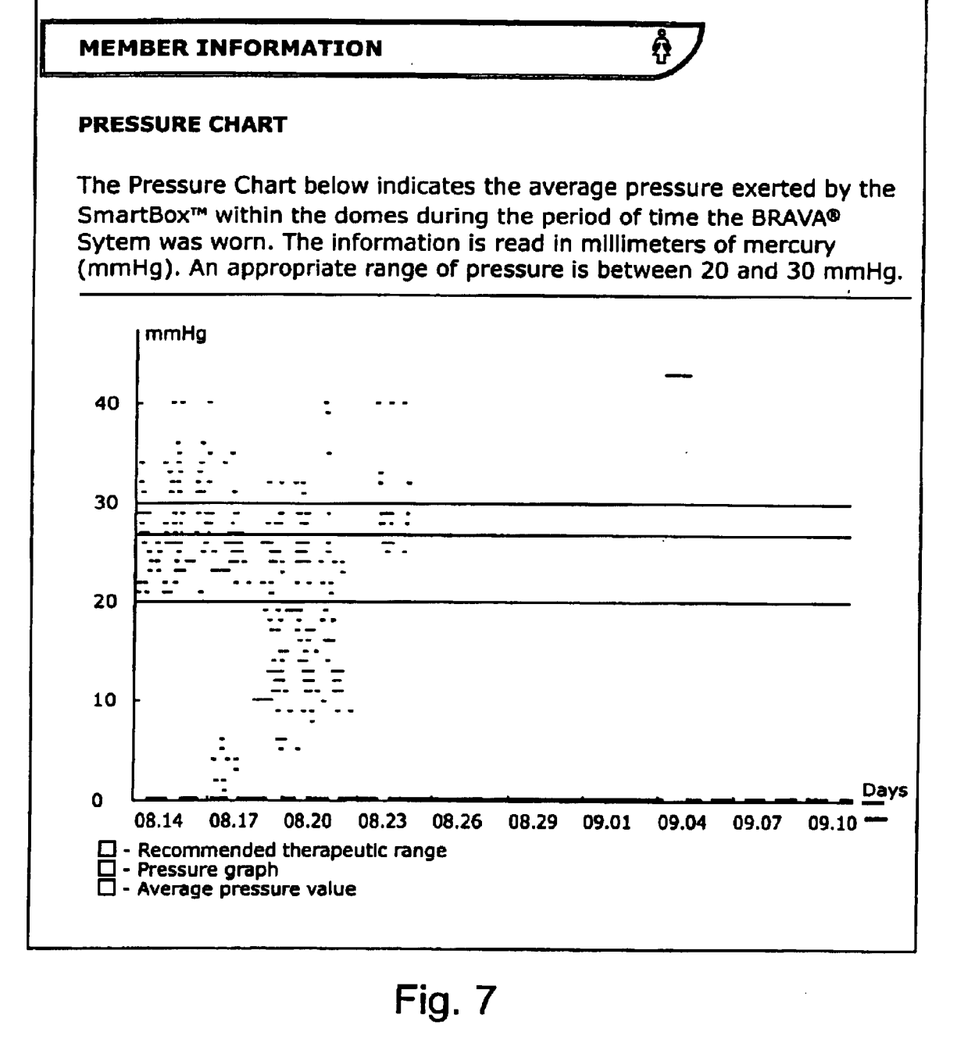
FIG. 7 is a portion of a page on the website showing a pressure chart relating to the patient's compliance.
Figure 8:
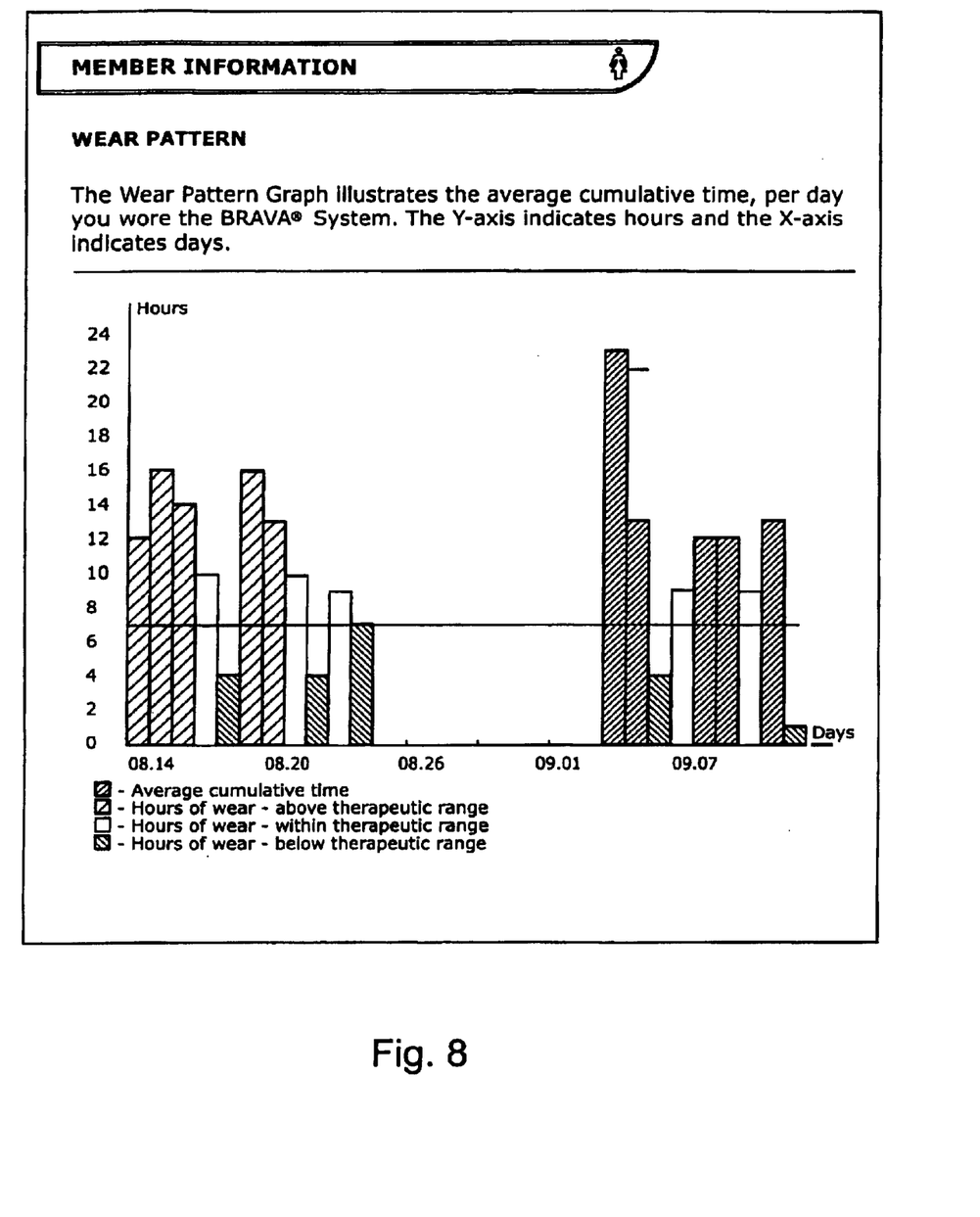
FIG. 8 is a portion of a page on the website showing a wear pattern bar chart relating to the patient's compliance.
Figure 9:
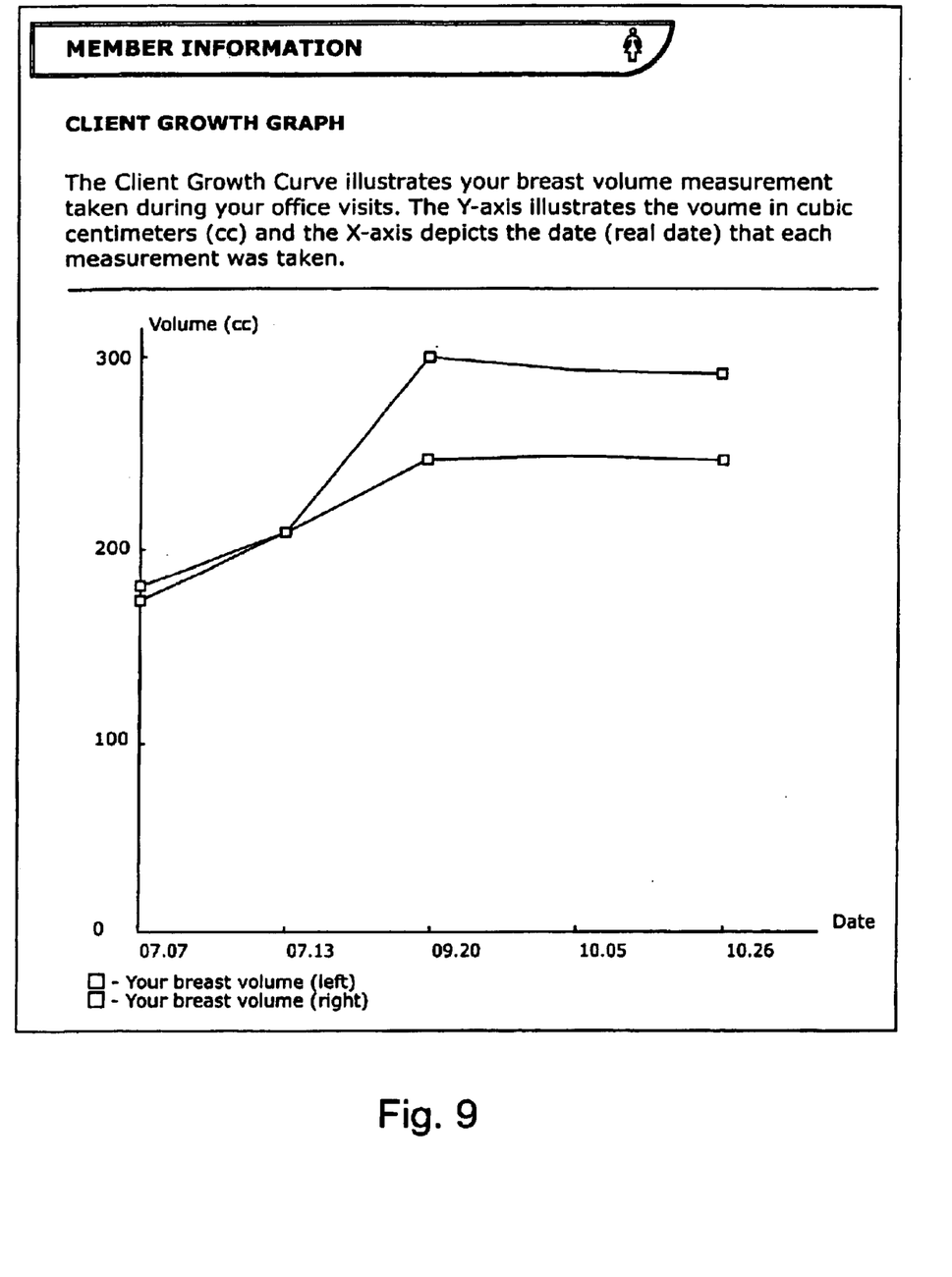
FIG. 9 is a portion of a page on the website showing a graph of patient breast size resulting from the patient's compliance.
Figure 10:
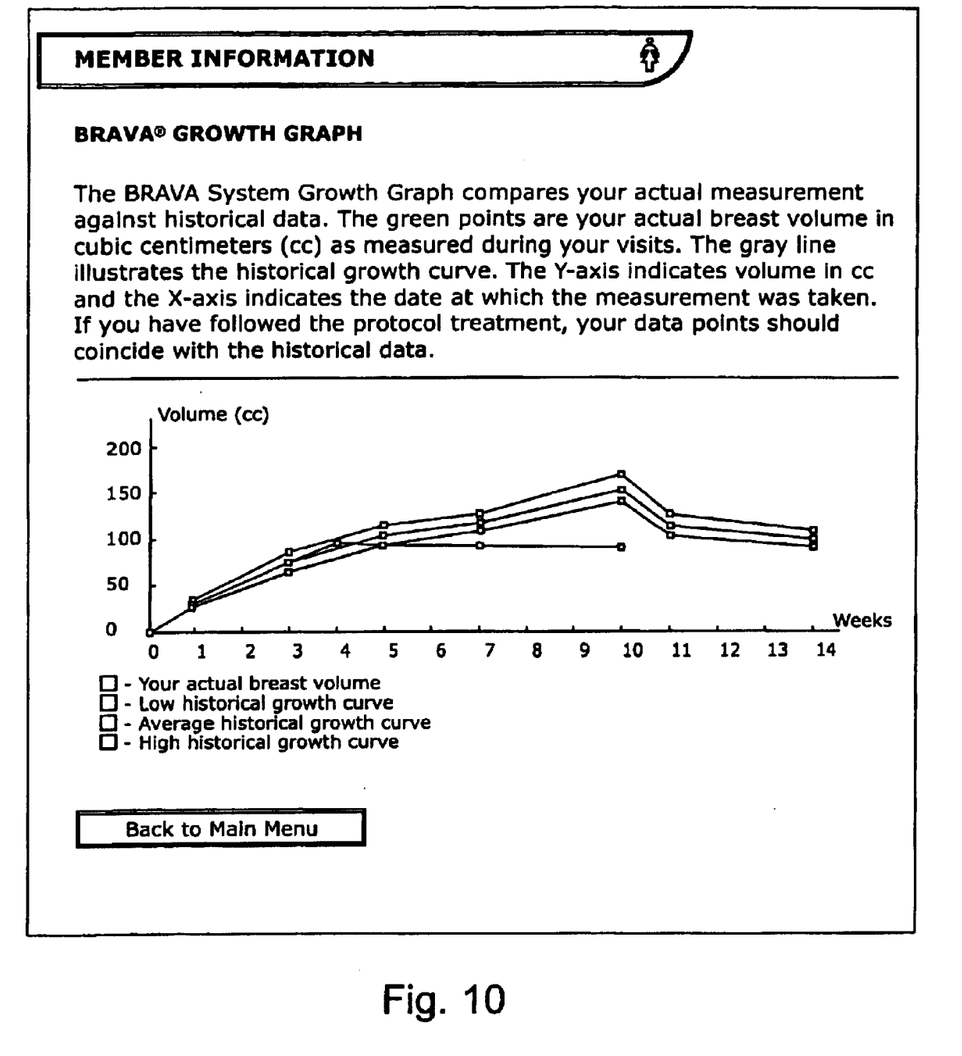
FIG. 10 is a portion of a page on the website showing a graph of a patient's individual performance as compared with average performance history.
Figure 11:
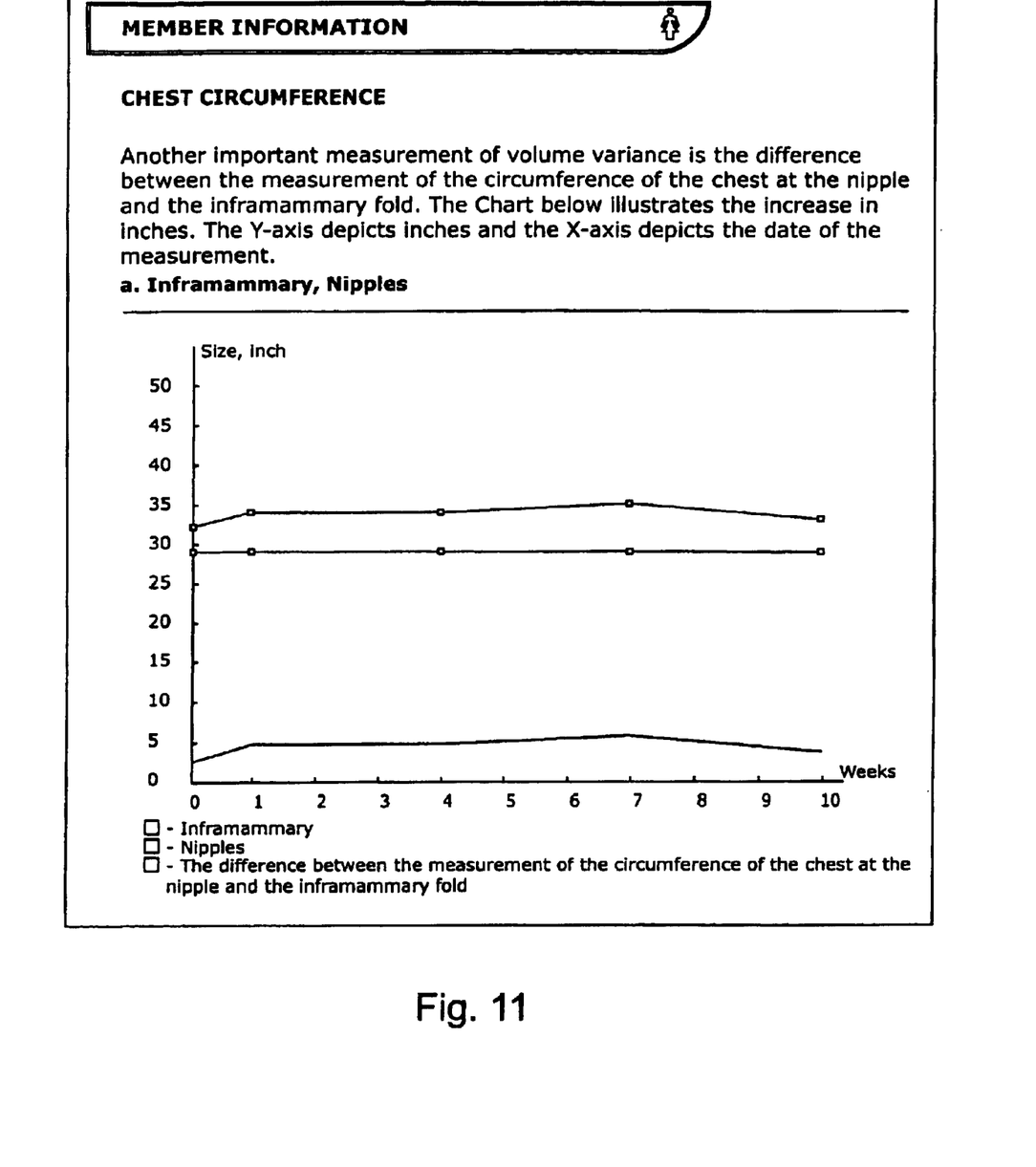
FIG. 11 is a portion of a page on the website showing a chart of a patient's chest circumference resulting from the patient's compliance.
Figure 12:
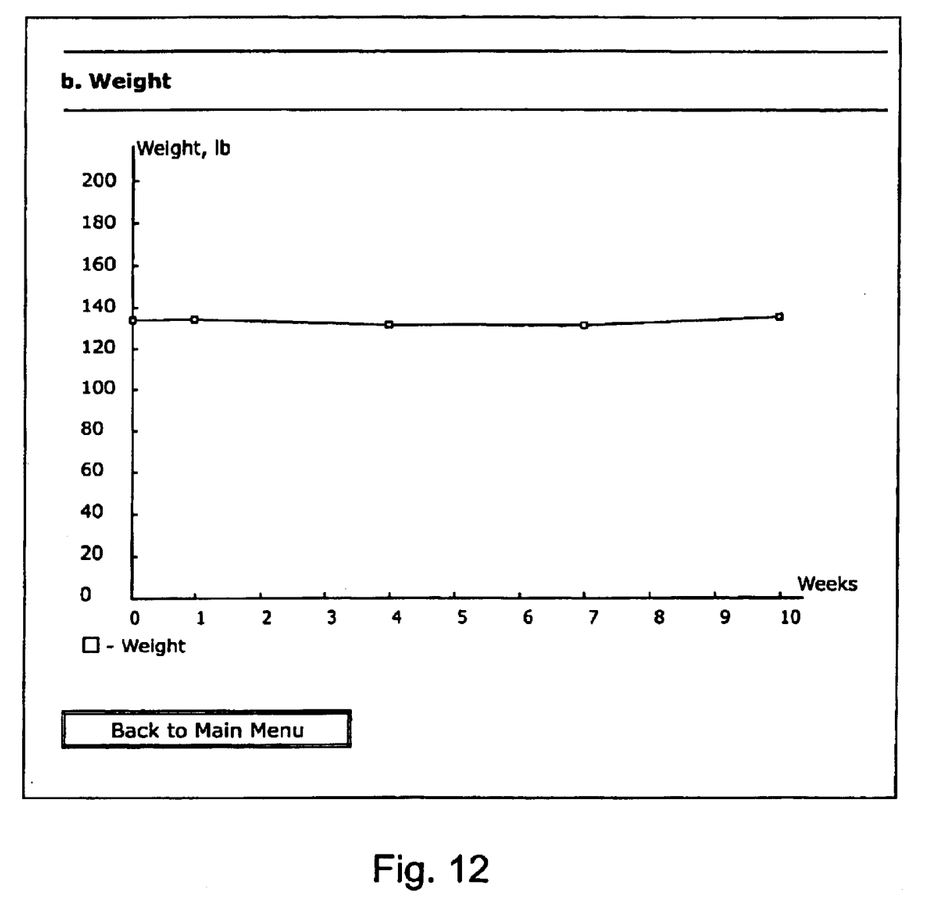
FIG. 12 is a portion of a page on the website showing a patient's weight as the protocol proceeds through various weeks of use.
Figure 13:
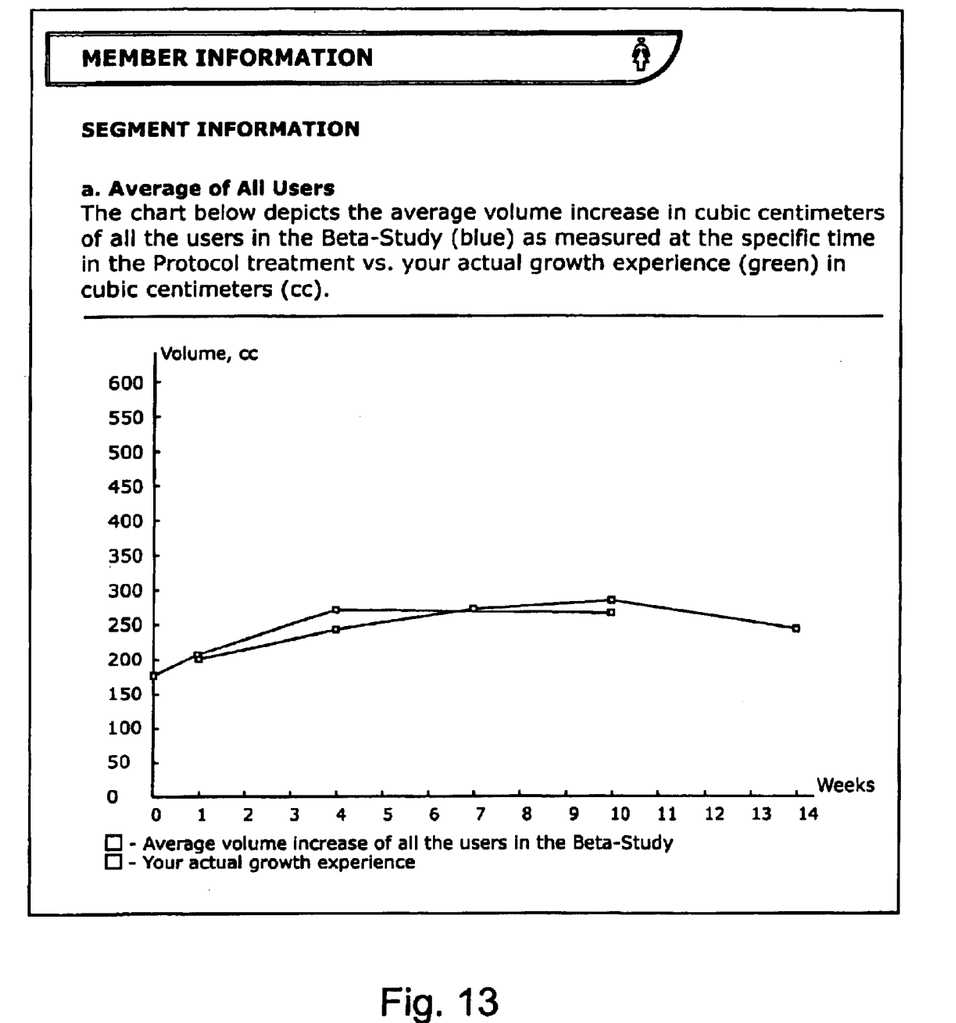
FIG. 13 is a portion of a page on the website showing a chart of average volume increase of all users of the device versus the individual patient's actual growth experience.
Figure 14:
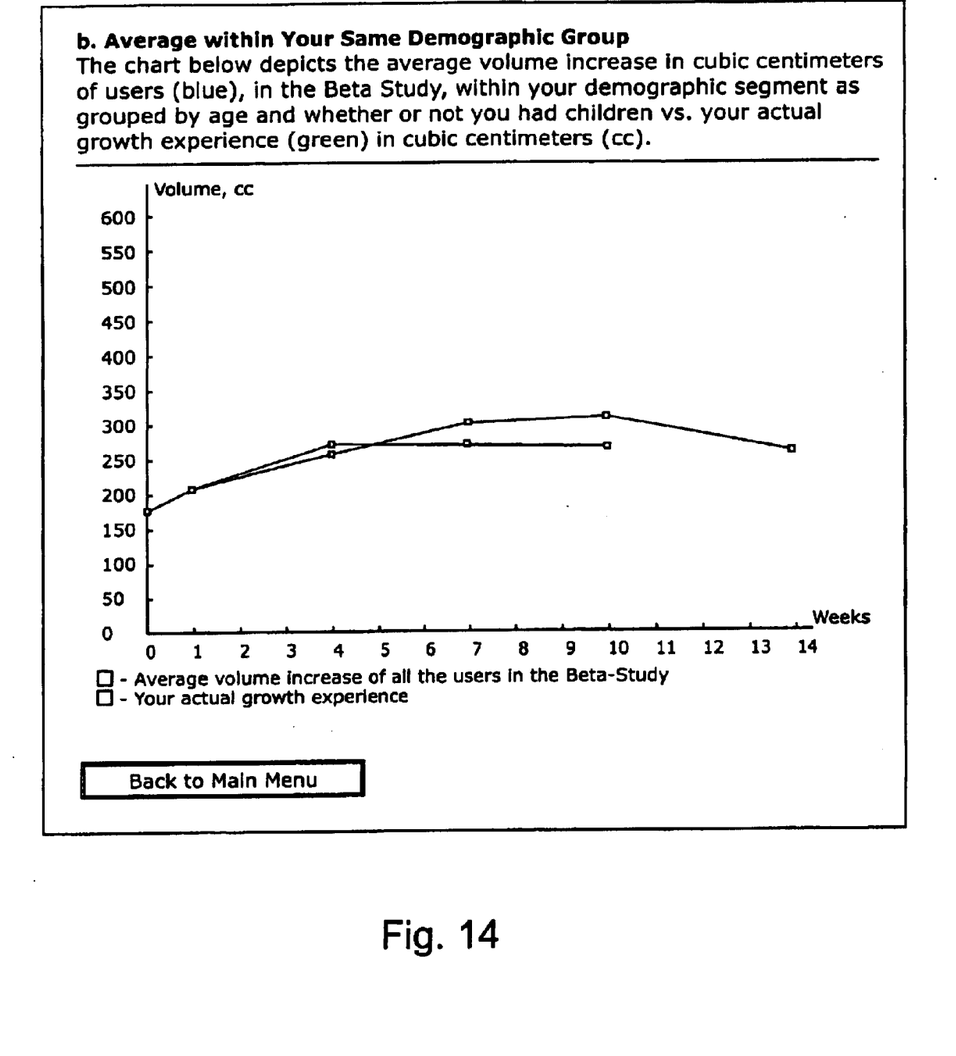
FIG. 14 is a portion of a page on the website showing a patient's volume increase compared with the average volume increase for patients within the same demographic group.

A web site may be arranged for displaying the data in a secure manner to patients as well as medical professionals. The website may comprise a typical home page introducing the user to the web site and allowing further navigation therefrom. A second page linked to the home page may be arranged as a sign on or log in page requiring a log in name and password which provides the security for access to the rest of the web site. Another page of the website may be arranged to ask for the user to select a doctor to display patients or other information. Another page allows a search by patient name or Smartbox number in order to find and display data relating to a particular patient, including treatment start and finish dates Another page asks for the user to select which information is desired to be displayed from a menu of various information including personal information, general medical information, demographics, baseline information, treatment history information, etc. Another page, which may linked to the information menu page maybe arranged to display information relating to the patient's first day of treatment and provides baseline information. Another page may be arranged to provide results information relating to patient compliance. Other pages on the website may be arranged for viewing by an individual patient and for providing individual feedback relating to that particular patient's compliance as well as a listing of other available information for selection to be viewed. For instance, as shown in FIG. 7, the website may illustrate a pressure chart for presenting the data to the patient relating to their individual compliance. As shown in FIG. 8, another page may be a wear pattern bar chart illustrating individual patient compliance data. As shown in FIG. 9, another page may illustrate the patient's breast size as measured by the medical professional during the patient's office visit, and the increased breast size resulting from the patient's compliance. As shown in FIG. 10, another page may illustrate and compares on a graph the patient's individual performance as compared with average performance history. As shown in FIG. 11, another page may illustrate in chart format a patient's chest circumference and another page (FIG. 12) may illustrate the patient's weight as the protocol proceeds through various weeks of use. Another of the website (FIG. 13) may be arranged to illustrate in chart fashion the average volume increase of all users of the device versus the individual patient's actual growth experience. Another page of the website (FIG. 14) may be arranged to illustrate the individual patient's volume increase compared with the average volume increase for patients within the same demographic group. Other pages of the website may be arranged to illustrate reports to the patient relating to their individual performance and to provide additional information available to the patient.

Through the web pages, the individual patient's compliance data may be processed and presented for viewing by the individual patient as well as her medical professional in a manner which is very informative with secure access guaranteeing privacy of the data. Furthermore, this data may be provided virtually instantaneously as the data is automatically downloaded through the Smartbox being placed in the cradle by the patient which then automatically transmits the data back to the network which itself may immediately process the data and update the data files for viewing over the Internet. With this arrangement, a patient is encouraged to download her data and to immediately get the feedback available to her through rapid processing of that data. In this way, a patient is provided information almost immediately after it is collected relating to her compliance and her progress through use of the medical device. This form of automatic data collection and presentation in an immediate manner back to the patient is highly desirable as it encourages patient compliance and ensures data integrity.

The medical professional preferably has the capability to enter data directly in the web site. This data entry makes it easy for the doctor to post the data obtained from the patient during her visit. Thus, the web site is interactive to a certain extent, at least for the doctor. By refusing this same feature to the patient, data integrity is assured.

Various changes and modifications of the various aspects of this invention would be apparent to those of skill in the art. These changes and modifications are intended to be included as part of the invention. For example, different medical devices may readily be utilized as part of the invention. Furthermore, while the inventors have preferably used an SQL server, assigning all of the smart boxes a unique identification number which is used along with sales and user documents to create a virtual patient folder, other methodologies may well be utilized to establish and maintain individual data files for patients. Furthermore, the data selected to be included is deemed to be relevant by the inventors for this particular medical device, although additional and varying kinds and forms of data may well be determined to be important and useful in other applications. Still another aspect of the Internet web site is that users including patients are only permitted to view data contained within the web site while medical professionals, including doctors, have the ability to input data directly, such data corresponding to measurement data and other data taken from the patient at the time that the patient visits the doctor. An ethernet network is shown for use in establishing a LAN at the central site. However, those of ordinary skill in the art realize that other kinds of communication or network protocols may be used to achieve the same results. Furthermore, while the Internet has been chosen as the preferable access link for the patient and doctor, a dial up network connection may be permitted or any other connection protocol as would be viewed as convenient and cost efficient by the users. Still other changes and modifications would be apparent and these are all intended to be included within the scope of the invention which should be viewed as limited only by the scope of the claims appended hereto and their legal equivalents.

What is claimed is:

1. A portable medical device adapted for applying a tensile force to a patient's soft tissue and having a control for automatically collecting and processing information relating to patient compliance with a recommended treatment protocol when said medical device is applied to said patient's soft tissue, and a separate communication cradle, said cradle being configured to connect to said control and having a communications link to thereby transmit said patient compliance information to a host.

2. The medical device of claim 1 wherein said communications link comprises an Internet connection.

3. The medical device of claim 2 wherein said control includes a battery and said cradle includes a battery charger, said battery charger being connected in circuit with the control battery when said control is connected to the cradle for charging thereof.

4. The medical device of claim 2 wherein said control has a micro-controller including a microcomputer for controlling its operation.

5. The medical device of claim 4 wherein said microcomputer further comprises a memory for storing the patient compliance information.

6. The medical device of claim 5 wherein said control further comprises a sensor for monitoring patient compliance and an alarm, said microcomputer being programmed to sound said alarm in response to an indication of non-compliance by the patient.

7. The medical device of claim 6 wherein the control further comprises an input to permit the patient to disable the alarm.

8. The medical device of claim 7 wherein the cradle further comprises an indicator for indicating a relative measure of patient compliance to the patient.

9. A portable medical device adapted for applying a tensile force to a patient's soft tissue and having a control for automatically collecting and processing information relating to patient compliance with a recommended treatment protocol when said medical device is applied to said patient's soft tissue, said control being configured to connect to a communications link to thereby transmit said patient compliance information to a host.

10. The medical device of claim 9 wherein said control further comprises a micro-controller, said micro-controller including a microcomputer.

11. The medical device of claim 10 further comprising a sensor connected to the microcomputer for sensing patient compliance.

12. A method for collecting data corresponding to patient compliance with a recommended protocol for wearing a medical device, the method comprising the steps of providing a portable medical device adapted for applying a tensile force to a patient's soft tissue, said medical device having a sensor for sensing when said device is being operatively worn by a patient wherein said sensor enables said medical device to automatically collect and process said patient compliance data when the medical device is applied to said patient's soft tissue, providing a communication connection for transmitting data from said device over a communication link, and providing a data collector in the portable medical device for collecting and processing information relating to patient compliance with the recommended treatment protocol, said data collector being adapted to receive data over said communication link transmitted by said communication connection.

13. The method of claim 12 further comprising a cradle, the communication connection being located within the cradle, and wherein the method further comprises the step of placing the device in the cradle for transmitting data.

14. The method of claim 13 wherein said data collector further comprises a digital data processor, and the method further comprises the steps of processing the data by the digital data processor and providing restricted access to said processed data by at least said patient.

15. The method of claim 14 wherein said communication link comprises the Internet, wherein the step of providing restricted access to said processed data includes the step of providing a restricted access web site on the internet which at least the patient can access to view his processed data.

16. The method of claim 15 wherein the step of providing a restricted access web site includes the step of providing restricted access to a medical professional for all of the processed data on the web site relating to a number of patients.

17. A method for collecting data relating to a patient's compliance with a recommended regimen for usage of a medical device adapted for applying a tensile force to a patient's soft tissue and providing feedback to said patient relating to said compliance, said method comprising the steps of providing a sensor in said medical device for sensing operative use of said medical device as the medical device is applied to said patient's soft tissue, communicating data corresponding to said operative use to a digital data processor, processing patient use data, and providing restricted access to said processed patient use data by said patient.

18. The method of claim 17 further comprising a cradle for receiving said medical device, and wherein the step of communicating data includes placing the medical device in the cradle.

19. The method of claim 18 wherein the step of providing restricted access to said processed patient use data includes the step of posting the processed patient use data on a restricted access Internet web site.

20. The method of claim 19 wherein the step of providing restricted access to said processed patient use data includes the step of providing restricted access to a medical professional for his patients.

21. A portable medical device adapted for applying a tensile force to a patient's soft tissue and having a control for automatically collecting and processing information relating to patient compliance with a recommended treatment protocol when said medical device is applied to said soft tissue, and a cradle separate from the medical device for receiving and operatively connecting to the control of said medical device as said medical device is placed therein, said cradle having a communications link which is activated upon placing the control for the medical device therein, said communications link being adapted to activate and transmit data contained within the control to a predetermined destination over the communications link.

22. The medical device of claim 21 wherein the communications link comprises a link to the Internet.

23. The medical device of claim 22 wherein the control is separable from the medical device for placing in the cradle.

24. The medical device of claim 23 wherein the control includes a microcomputer and at least one sensor connected thereto, said microcomputer having a memory for storing data received from said at least one sensor.

25. The medical device of claim 24 wherein the communications link includes a modem and a telephone port for connection to a telephone line for transmitting data over the telephone line to said predetermined destination.

26. The medical device of claim 25 wherein said predetermined destination includes at least one server, and wherein said server is connected to the Internet at least intermittently and hosts a web site for displaying the patient compliance information.

27. The medical device of claim 26 wherein the medical device is a plurality of medical devices that are each connectable to their respective cradles for transmitting data to the at least one server, and said server web site is configured to display data for each patient using the medical device.

28. The medical device of claim 27 wherein said web site has a security layer for restricting access to said web site.

* * * * *